United States Patent [19]

Bilitch

[11] 4,256,115

[45] Mar. 17, 1981

[54] LEADLESS CARDIAC PACER

[75] Inventor: Michael Bilitch, Los Angeles, Calif.

[73] Assignee: American Technology, Inc., Northridge, Calif.

[21] Appl. No.: 111,776

[22] Filed: Jan. 14, 1980

Related U.S. Application Data

[63] Continuation-in-part of Ser. No. 752,266, Dec. 20, 1976, abandoned, and a continuation of Ser. No. 921,703, Jul. 3, 1978, abandoned.

[51] Int. Cl.³ .............................................. A61N 1/36
[52] U.S. Cl. ................................ 128/419 P; 178/785
[58] Field of Search ......... 128/419 E, 419 P, 419 PG, 128/419 PS, 784, 785

[56] References Cited

U.S. PATENT DOCUMENTS

| | | | |
|---|---|---|---|
| 3,543,761 | 12/1970 | Bradley | 128/419 E |
| 3,835,864 | 9/1974 | Rasor et al. | 128/419 P |
| 3,926,198 | 12/1975 | Kolenik | 128/419 PG |

FOREIGN PATENT DOCUMENTS 507325  4/1976  U.S.S.R. ............................... 128/419 P

OTHER PUBLICATIONS

Schuber et al. "Transactions of the American Society for Artificial Internal Organs", vol. 10, 1964, pp. 366–369.

*Primary Examiner*—William E. Kamm
*Attorney, Agent, or Firm*—Vernon D. Beehler

[57] ABSTRACT

A leadless battery operated cardiac pacemaker is embodied in a small disc-like case for attachment beneath the pericardium directly to the heart muscle. One electric lead is curled and serves also as a means for both physically and electrically attaching the case to the heart muscle. The other lead surrounds the one lead and is drawn into surface to surface electric contact with body tissue to close the circuit. Solid state redundant circuitry makes provision to serve as a safety feature against possible malfunction.

9 Claims, 6 Drawing Figures

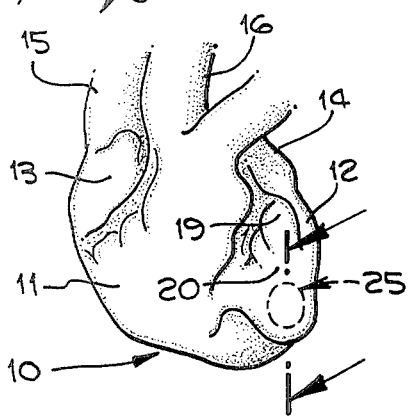
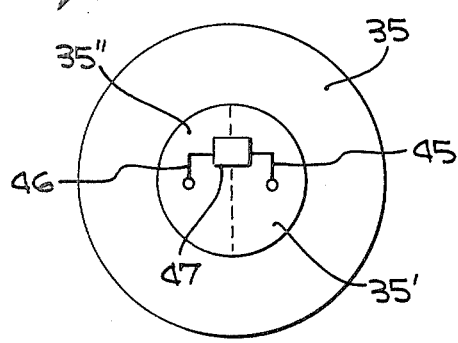
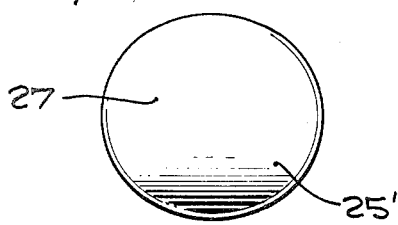
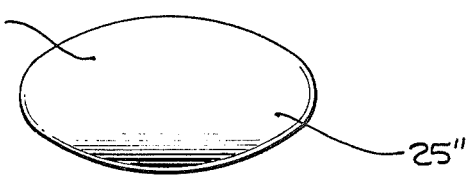
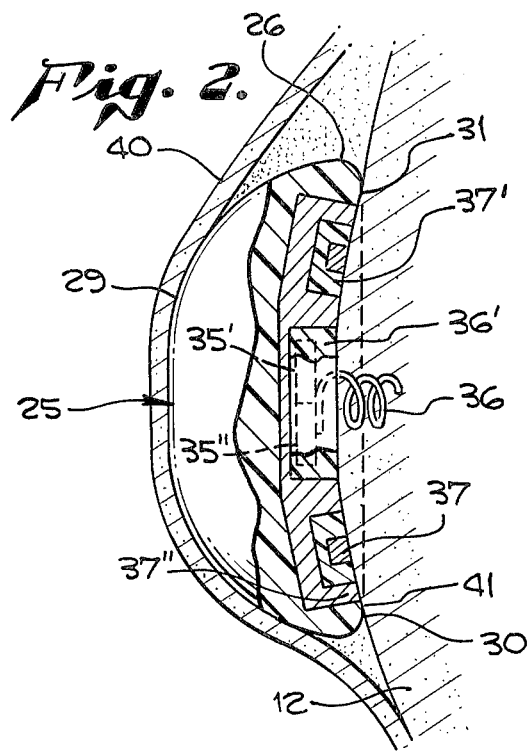
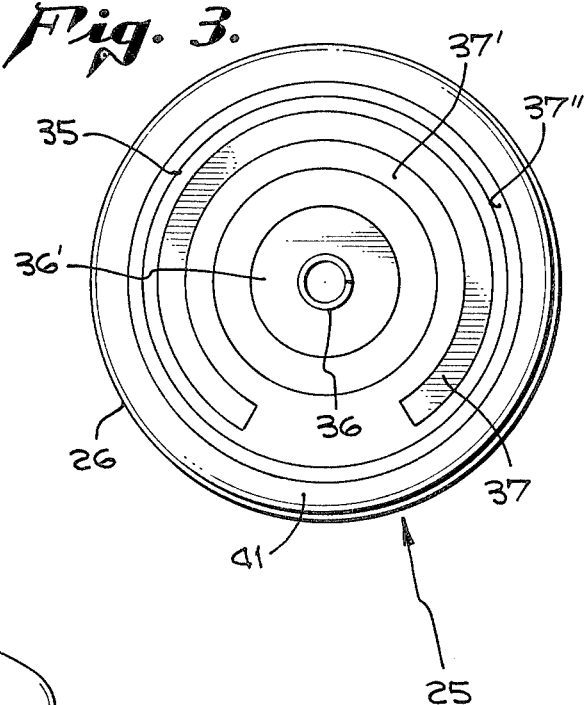

LEADLESS CARDIAC PACER

This is a continuation-in-part of application Ser. No. 752,266, filed Dec. 20, 1976, now abandoned, and a continuation of Ser. No. 921,703, filed July 3, 1978, now abandoned.

Conventional cardiac pacemakers are commonly housed in a polished titanium or stainless steel or epoxy jacket which measures four or five centimeters wide, six to eight centimeters high, and at least one and one-half centimeters thick. The contents of such cases including battery, solid state electronics with appropriate circuitry and necessary leads has considerable weight and the entire weight must be supported by body tissues when the case is implanted into the chest of the user.

Further still, plastic encased wire leads several inches in length must be connected to the pacemaker circuitry in an especially cautious fashion to be certain of continued performance over many years and also to be certain to exclude body fluids which would cause the connections to deteriorate. The leads are such that they must either, one: enter one of the veins, and follow through the vein to the location where the vein connects with the heart muscle, or two: enter the chest cavity between or below the ribs to enter the chest cavity and the pericardial space to attach to the outer surface of the heart. As necessary as such leads may be to operation of a battery powered cardiac pacemaker, such leads nevertheless are foreign substances in the body and have that objectionable feature. Also, when for any reason the packmaker must be serviced or replaced, leads must be disconnected and reconnected, and often withdrawn and replaced. This obviously involves surgery and usually surgery of a very major and delicate nature.

Another difficulty with the employment of an electric lead is the need for providing an acceptable, dependable connection from the electric lead to the mechanism of the pacemaker unit. The pacemaker unit heretofore has been one of some appreciable weight, at least from the point of view of needing to be carried by the muscles of the body in the chest area. Some movement is bound to take place as the patient must move his body physically, and there is inevitably a degree of movement where the lead makes connection with the pacemaker case. A predictable feature of all leads is that they are subject to displacement and fracture with consequent cessation of effective active pacing.

It is therefore among the objects of the invention to provide a new and improved leadless pacemaker of a size and type capable of being connected directly to the heart muscle.

Another object of the invention is to provide a new and improved leadless pacemaker in which is incorporated electric contacts which are applied directly to the heat muscle so that the pacemaker can be implanted within the pericardial sac in the closest proximity possible to the heart muscle which needs to be controlled.

Still another object of the invention is to provide a new and improved leadless pacemaker of such a design and construction that it can be applied in snug relationship with respect to the heart muscle which it serves, which makes use of the connecting means as a means of physical attachment of the pacemaker in proper position, and which further is of such character that it can be supported in part by the pericardial sac tissue once it is implanted, thereby to ease the burden of support.

Still further among the objects of the invention is to provide a new and improved leadless cardiac pacemaker which is so equipped that should the initial pacemaker mechanism malfunction for any reason, an automatic switch can be made to a redundant circuitry for the purpose of immediately taking over servicing of the heart muscle.

Further included among the objects of the invention is to provide a new and improved leadless pacemaker of compact construction, the case of which can be formed so as to snugly accommodate itself to the surface of the heart muscle to which it is attached, thereby to improve the physical comfort of the device when worn as well as to assure the necessary dependable electric contact between the pacemaker and the heart muscle which it services.

With these and other objects in view, the invention consists of the construction, arrangement, and combination of the various parts of the device, whereby the objects contemplated are attained, as hereinafter set forth, pointed out in the appended claims and illustrated in the accompanying drawings.

FIG. 1 is a generalized drawing of a typical human heart showing one location for the leadless cardiac pacer.

FIG. 2 is an enlarged sectional view taken on the line 2—2 of FIG. 1.

FIG. 3 is a bottom view of the pacer.

FIG. 4 is a plan view showing a leadless pacer of slightly different shape.

FIG. 5 is a plan view of a leadless pacer of still another shape.

FIG. 6 is a schematic plan view of a redundant system.

In an embodiment of the invention chosen for the purpose of illustration there is shown in FIG. 1 a typical human heart 10, portions of which locate a right ventricle 11, a left ventricle 12, a right auricle 13, and a left auricle 14. Also shown are a superior vena cava 15, the aorta 16, the pulmonary artery 17, the coronary artery 18, cardiac vein 19, and epicardium 20. The view shown in FIG. 1 is the anterior view.

In the chosen embodiment a housing 25 for the leadless cardiac pacer is shown adjacent the left ventricle 12 as the heart muscle to which the leadless pacer is to be applied. Relative sizes of the housing 25 and the epicardium are substantially as shown in FIG. 1.

FIG. 3 shows a case 25 with a perimeter 26 which is substantially circular. As shown, however, in FIG. 4, a perimeter 27 of a case 25' may have the form of a full rounded ellipse or as shown in FIG. 5 a perimeter 28 of a case 25" may be that of a relatively flat ellipse.

The body of the case is contained between an outer face 29 and an inner face 30. The outer face 29 is convexly rounded, and the roundness extends around the perimeter 26 to a junction with the inner face 30 which is preferably cupped, thereby to provide a gently rounded rim 31.

The major portion of the housing may consist of an inert synthetic plastic resin or a material such as titanium or stainless steel, namely a tissue compatible material. For good results the housing can be approximately 3.8 centimeters or less from side to side, about 1 centimeter thick at the mid-portion, and cupped for a depth of about 0.2 centimeter. Complete and ready for installation, the case and its contents should weigh no more than 50 grams. The precise dimensions and weight depend on currently available semi-conductor or solid state technology.

The electronics and power source is contained as a unit within a somewhat cylindrical housing 35, encapsulated in the case 25, adjacent the inner face 30, and centrally disposed relative to the perimeter 26. A cathode 36 has the form of a resilient helicoid about 0.4 centimeter long and with coils of about 0.4 centimeter in diameter, there being provided about 2½ turns in the embodiment illustrated. An anode 37 is arcuate in form as shown in FIG. 3 surrounded by tissue compatible insulating bands 37' and 37". A tissue compatible band 36' also surrounds the cathode 36 in which it may be embedded. Although the anode 37 is shown to be arcuate on the inner face 30, other locations and shapes may be acceptable where contact can be made with the body tissue. All parts within the case are hermetically sealed. It is important that the insulating bands be wide enough to avoid added current drain which, under some circumstances may require the anode to be close to the perimeter of the case 25.

Of further consequence is the size of the housing 35 which preferably extends transversely, with respect to FIG. 3, a distance of approximately 1 centimeter, the depth of which is preferably less than about one-half the depth of the case 25. By making the anode 37 about 0.2 centimeter wide, the width of the space 38 is adequate for insulating purposes between the two electric contacts, and the anode provides an abundant contacting surface for engagement with the heart muscle. The cathode on the other hand, being a helicoid, penetrates the muscle of the left ventricle 12 for a distance of about 0.4 centimeter, namely, the length of the helicoid, assuring good electric contact.

As previously noted, the mass of the assembly comprising the case 25 and housing 35 may be as much as 50 grams but preferably less, and with a specific gravity of 1.0 plus or minus 15 percent.

For implantation the pericardium 40 is cut surgically to permit access to the heart muscle, and the case is then inserted beneath the pericardium substantially as shown in FIG. 2 and the helicoid rotated into engagement with the heart muscle. This attachment serves a double purpose, namely, making electric contact between the electronics of the housing 35 and the heart muscle and also physically attaching the leadless pacer to the heart muscle. By making a sling of the pericardium, additional support is provided for the case. Moreover, having the inner face 30 cupped as shown permits the inner face together with the anode and the material of the case 25 and housing 35 to lie flat against the surface of the heart muscle. By following the dimensions suggested, there is an annular area 41 of contact between the perimeter of the case 25 and the heart muscle, the area having a width of about 0.5 centimeter.

Because the leadless pacemaker is implanted entirely within the pericardium and there is inevitably the possibility of operation in a manner not productive of needed results in a particular installation resort is had to a solid state system or multiple redundant system supplied by a conventional power source 48 in the case. Within the housing 35, instead of a single unit there are provided two or more integrated circuits or chips 35' and 35", both complete in their circuitry for operation with the cathode 36 and anode 37. Only two systems are shown by way of example but a multiple number may be used in actual practice. Leads 45 and 46 respectively from the chips 35' and 35" connect to a transistor relay 47 programed to switch operation from the chip 35' where that is the initially operating circuit to the chip 35" in event there may be any malfunctioning of the circuitry of the chip 35'. By resort to necessary conventional electronics, the need for switching over is promptly detected and a switch over accomplished automatically. The leads and the transistor relay are encapsulated within the case or, if need be, within the housing 35.

Having described the invention, what is claimed as new in support of Letters Patent is as follows:

1. A leadless cardiac pacemaker for attachment to a heart muscle on the exterior surface beneath the pericardium, said pacemaker comprising a case of tissue compatible material having a circumferentially rounded perimeter presenting respective outer and inner faces, said case having a smooth imperforate surface throughout its exterior with the inner face adapted to contact the heart muscle and having an area smaller than the area of the contacted portion of the heart muscle, an annular perimetrical area between said faces being transversely arcuate, a solid state electronic pacer circuitry unit including a solid state power source hermetically encapsulated in said case, a cathode centrally mounted in fixed position on said inner face, said cathode comprising a contact wire with a section thereof exterior to the case being bare, said wire having a captive end in fixed position on one face of said case and electrically connected to said unit, said bare section comprising a tissue penetrating and fastening strand of material having an overall length exceeding the width by many times and projecting outwardly of said case, the penetrating and fastening strand being of resilient character and having a muscle penetrating tip whereby upon insertion into the heart muscle the penetrating and fastening portion draws the case against the exterior of the heart muscle, and anode with an exposed portion surrounding said cathode and in fixed position on the same face of said case as said cathode, said anode comprising a tissue contacting area mounted on the inner face of the case and in position flush with said inner face and being electrically connected to said unit, there being an area of dielectric material on the case forming a part of said inner face separating said anode and said cathode.

2. A leadless cardiac pacemaker as in claim 1 wherein said inner face is concave and the area of said inner face on both sides of said anode comprises dielectric material.

3. A leadless cardiac pacemaker as in claim 2 wherein the maximum transverse dimension of said case is about 3.8 centimeters, the breadth of said anode is about 0.2 centimeter, and the area on each side of said anode is about 0.4 centimeter.

4. A leadless cardiac pacemaker as in claim 1 wherein the depth of the case is about one-third the maximum transverse dimension, the inner face is concave with a depth of about 0.2 centimeter at the center and the mass is less than 50 grams.

5. A leadless cardiac pacemaker as in claim 1 wherein said cathode comprises both a single electric contact and the sole fastening means between said case and the interior of the heart muscle.

6. A leadless cardiac pacemaker as in claim 1 wherein said tissue penetrating and fastening portion comprises a helicoid of bare conducting material throughout its exposed length.

7. A leadless cardiac pacemaker as in claim 6 wherein the helicoid comprises about two and one-half turns having a length of about 0.4 centimeter and a diameter of about 0.4 centimeter.

8. A leadless cardiac pacemaker as in claim 6 wherein said helicoid comprises the sole attachment means for said pacemaker to the heart muscle and the sole electric contact for said cathode, said helicoid being adapted throughout its entire length to be embedded in the heart muscle when the adjacent inner face of the case is in engagement with the exterior of the heart muscle.

9. A leadless cardiac pacemaker installation for a human heart at a location between the exterior of a wall of the heart and the pericardium, said installation including a case of tissue compatible material having a circumferentially rounded perimeter presenting respective outer and inner faces and a thickness substantially less than the minimum transverse dimension, said case having an annular transversely arcuate perimetrical area between said faces, the entire surface of said faces and the perimetrical area therebetween being smooth and imperforate, a solid state electronic pacer circuitry unit including a solid state power source hermetically encapsulated in said case, a cathode centrally mounted in fixed position on said inner face, said cathode comprising a contact wire with a helicoid bare section thereof exterior to the case, said wire having a captive end in fixed position in said case and electrically connected to said unit, said helicoid bare section being a tissue penetrating and fastening portion with an overall length projecting outwardly of the case and extending partway through the wall of the heart, an anode with an exposed portion surrounding said cathode and in fixed position on the case and relative to said cathode, said anode comprising a tissue contacting area mounted on the same face as said cathode and in position flush with said inner face and in engagement with the wall of the heart, said anode being electrically connected to said unit, said case having a position lodged in a space between the pericardium and the wall of the heart with the pericardium in engagement with the outer face of the case.

* * * * *